(12) United States Patent
Kovacs

(10) Patent No.: US 7,150,997 B2
(45) Date of Patent: *Dec. 19, 2006

(54) MULTIPLEXED ACTIVE BIOLOGIC ARRAY

(75) Inventor: Gregory T. A. Kovacs, Stanford, CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/081,123

(22) Filed: Mar. 15, 2005

(65) Prior Publication Data

US 2005/0155863 A1    Jul. 21, 2005

Related U.S. Application Data

(63) Continuation of application No. 09/903,110, filed on Jul. 10, 2001, now Pat. No. 6,682,936, which is a continuation of application No. 09/364,676, filed on Jul. 30, 1999, now Pat. No. 6,258,606, which is a continuation of application No. 08/677,305, filed on Jul. 9, 1996, now Pat. No. 5,965,452.

(51) Int. Cl.
G01N 27/27       (2006.01)
G01N 27/26       (2006.01)
G01N 27/327      (2006.01)
G01N 27/453      (2006.01)
G01N 21/01       (2006.01)

(52) U.S. Cl. ............... 436/149; 204/412; 204/413; 422/82.01; 422/82.02; 422/82.03; 436/73; 436/79; 436/86; 436/89; 436/93; 436/94; 436/95; 436/106; 436/107; 436/108; 436/111; 436/127; 436/128; 436/131; 436/150; 436/151; 436/164; 436/172; 436/501; 436/518

(58) Field of Classification Search ............... 422/68.1, 422/82.01–82.03, 82.05; 204/412–413; 436/73, 436/79, 86–90, 93–95, 106–113, 164, 127–132, 436/149–151, 172, 501, 503, 508, 512–513, 436/518, 527
See application file for complete search history.

(56) References Cited

U.S. PATENT DOCUMENTS 3,430,072 A    2/1969   Stevens (Continued)

FOREIGN PATENT DOCUMENTS

EP      0376611 A2    7/1990

(Continued)

OTHER PUBLICATIONS

Connolly, et al., "Microelectronic & Nanoelectronic Interfacing Techniques For Biological Systems", Sensors & Actuators B, 6, 1992, 113-121.

(Continued)

Primary Examiner—Arlen Soderquist
(74) Attorney, Agent, or Firm—O'Melveny & Myers LLP

(57) ABSTRACT

A method of addressing and driving an electrode array includes the step of addressing one or more electrodes within the array using a plurality of row and column lines. In one aspect of the method, a value corresponding to a voltage is stored in a local memory associated with each electrode. The addressed electrodes are then driven at the voltages corresponding to the stored values. In another aspect of the method, a driving element associated with each addressed electrode is selectively coupled with a voltage line so as to charge the electrode with the voltage on the voltage line. The device and methods may be used in the synthesis of biopolymers such as oligonucleotides and peptides.

28 Claims, 8 Drawing Sheets

U.S. PATENT DOCUMENTS

| | | | |
|---|---|---|---|
| 3,957,592 | A | 5/1976 | Young |
| 4,280,815 | A | 7/1981 | Oberhardt et al. |
| 4,772,851 | A | 9/1988 | Schattschneider |
| 4,787,963 | A | 11/1988 | MacConnell |
| 4,924,224 | A | 5/1990 | Takahasi et al. |
| 5,039,490 | A | 8/1991 | Marsoner et al. |
| 5,093,268 | A | 3/1992 | Leventis et al. |
| 5,178,161 | A | 1/1993 | Kovacs |
| 5,314,495 | A | 5/1994 | Kovacs |
| 5,341,215 | A | 8/1994 | Seher |
| 5,378,343 | A | 1/1995 | Kounaves et al. |
| 5,434,049 | A | 7/1995 | Okano et al. |
| 5,445,934 | A | 8/1995 | Fodor et al. |
| 5,475,213 | A | 12/1995 | Fujii et al. |
| 5,500,188 | A | 3/1996 | Hafeman et al. |
| 5,527,670 | A | 6/1996 | Stanley |
| 5,605,662 | A | 2/1997 | Heller et al. |
| 5,632,876 | A | 5/1997 | Zanzucchi et al. |
| 5,632,957 | A | 5/1997 | Heller et al. |
| 5,639,423 | A * | 6/1997 | Northrup et al. ............ 422/50 |
| 5,653,939 | A | 8/1997 | Hollis et al. |
| 5,849,486 | A | 12/1998 | Heller et al. |
| 5,891,630 | A | 4/1999 | Eggers et al. |
| 5,965,452 | A | 10/1999 | Kovacs |
| 6,017,696 | A | 1/2000 | Heller et al. |
| 6,048,690 | A | 4/2000 | Heller et al. |
| 6,051,380 | A | 4/2000 | Sosnowski et al. |
| 6,054,270 | A | 4/2000 | Southern |
| 6,066,448 | A | 5/2000 | Wohlstadter et al. |
| 6,258,606 | B1 | 7/2001 | Kovacs |
| 6,682,936 | B1 | 1/2004 | Kovacs |
| 6,867,048 | B1 | 3/2005 | Kovacs |

FOREIGN PATENT DOCUMENTS

| | | | |
|---|---|---|---|
| WO | 93/22678 | * | 11/1993 |
| WO | 95/12808 | * | 5/1995 |

OTHER PUBLICATIONS

Dees, et al., "Experimental Observations Of Free-Convection Mass Transfer To A Horizontal Surface With A Micromosaic Electrode", J. Electrochem. Soc., 134, 2, Feb. 1987, 369-377.

Eggers, et al., "A Microchip For Quantitative Detection Of Molecules Utilizing Luminescent & Radioisotope Reporter Groups", BioTechniques, Sep. 1994, 17, 516-520, 522, 524-525.

Fiaccabrino, et al., "Array Of Individually Addressable Microelectrodes", Sensors & Actuators B, 18-19, 1994, 675-677.

Fielden, et al., "Voltammetric Information From Arrays Of Individually Controlled Electrodes: Their Potential For Industrial Process Measurements", Analytica Chimica Acta, 273, 1993, 111-121.

Fuhr, et al., "Travelling Wave-Driven Mirocfabricated Electrohydrodynamic Pumps For Liquids", J. Micromech. Microeng., 4, 1994, 217-226.

Gray, et al., "MOS Operational Amplifier Design—A Tutorial Overview", IEEE Journal Of Solid-State Circuits, SC-17, 6, Dec. 1982, 969-982.

Harrington, et al., "Multiple Electrode Potentiostat", Rev. Sci. Instrum., 60, 10, Oct. 1989, 3323-3328.

Hermanson, et al., Immobilized Affinity Ligand Techniques, Academic Press, Inc., 1992, 410-417.

Hermes, et al., "An Amperometric Microsensor Array With 1024 Individually Addressable Elements For Two-Dimensional Concentration Mapping", Sensors & Actuators, B, 21, 1994, 33-37.

Hoogvleit, et al., "Multichannel Amperometric Detection System For Liquid Chromatography & Flow Injection Analysis", Anal. Chem., 63, 1991, 2418-2423.

Kakerow, et al., "A Monolithic Sensor Array Of Individually Addressable Microelectrodes", Sensors & Actuators A, 43, 1994, 296-301.

Livache, et al., "Preparation Of A DNA Matrix Via An Electrochemically Directed Copolymerization Of Pyrrole & Oligonucletides Bearing A Pyrrole Group", Nucleic Acids Research, 22, 15, 1994, 2915-2921.

Matsue, et al., "Multichannel Electrochemical Detection System For Flow Analysis", Anal. Chem., 62, 1990, 407-409.

Meunier, et al., "High-Accuracy Oxygen Polarograph For Photosynthetic Systems", Rev. Sci. Instrum, 59, 3, Mar. 1988, 486-491.

Meyer, et al., "Two-Dimensional Imaging Of $O_2H_2O_2$, & Glucose Distributions By An Array Of 400 Individually Addressable Microelectrodes", Anal. Chem., 67, 1995, 1164-1170.

Pentari, et al., "Construction & Applications Of A Microcomputer Cotrolled Pulsed Amperometric Detector System", Anal. Instrum, 15, 4, 1986, 329-345.

Reay, et al., "Microfabricated Electrochemical Analysis System For Heavy Detection", Sensors & Actuators B, 34, 1996, 450-455.

Tallman, et al., "A Wide Bandwidth Computer Based Potentiostat For Fast Voltammetry At Microelectrodes", J. Electroanal. Chem., 280, 1990, 327-340.

Taylor, Immobilized Antibody- and Receptor-Based Biosensors, 1991, 262-303.

Whitehurst, et al., "Actively-Scanned Microelectrode Arrays", 22nd Annual Meeting Of the Society For Neuroscience, 18, 1992, Abstract 22.24.

Yuhang, et al., "Microcomputer Controlled FFT Electrochemical Impedance Measurement System", Wuhan Daxue Xuebao, Ziran Kexueban, 1987, 65-71.

Zipper, et al., "Computer-Controlled Monitoring & Data Reduction For Multiple Ion-Selective Electrodes In A Flowing System", Anal. Chem., 46, 1974, 2111-2118.

* cited by examiner

DIRECT OPTICAL
PATH TO PHOTODETECTOR

DIRECT OPTICAL
PATH TO PHOTODETECTOR

MULTIPLEXED ACTIVE BIOLOGIC ARRAY

This Application is a continuation of U.S. application Ser. No. 09/903,110, filed on Jul. 10, 2001, now issued as U.S. Pat. No. 6,682,936, which is a continuation of U.S. application Ser. No. 09/364,676, filed Jul. 30, 1999, now issued as U.S. Pat. No. 6,258,606, which is a continuation of U.S. application Ser. No. 08/677,305, filed on Jul. 9, 1996, now issued as U.S. Pat. No. 5,965,452, all of which are incorporated by reference as if set forth fully herein.

FIELD OF THE INVENTION

The present invention relates generally to electronic systems for carrying out and/or monitoring biologic reactions and, more particularly, to the design, fabrication and uses of self-addressable, self-assembling microelectronic systems for carrying out and controlling multi-step and multiplex reactions in microscopic formats. In particular, these reactions include reactions such as nucleic acid hybridizations, nucleic acid amplification, sample preparation, antibody/antigen reactions, clinical diagnostics, and biopolymer synthesis, including, but not limited to, the synthesis of different oligonucleotides or peptides at specific electrode sites.

BACKGROUND OF THE INVENTION

For some time now, substantial attention has been directed to the design, implementation and use of array-based electronic systems for carrying out and/or monitoring biologic reactions.

For example, it has been recognized that electronic biosensors of various types may be used to monitor (or measure) the progress of certain biologic reactions, and that arrays of these sensors may be fabricated using techniques similar to those utilized in the integrated circuits field. As shown in FIG. 1, a typical prior art biosensor 1 may include a biospecific immobilization surface 2 having an immobilized affinity ligand 3 bound thereto, a transducer 4 capable of sensing the occurrence of chemical reactions which may occur between the immobilized ligand 3 and a specific analyte, and an amplification and control unit 5 for filtering, amplifying and translating signals generated by the transducer 4 into various measurements useful for monitoring the progress or occurrence of a selected biologic reaction. Biosensors of the type described above are discussed in some detail in *Protein Immobilization, Fundamentals & Applica-tions*, R. F. Taylor, ed. (1991) (chapter 8); and *Immobilized Affinity Ligand Techniques*, Hermanson et al. (1992) (chapter 5).

The fabrication of an array of biosensors is disclosed, for example, in U.S. patent application Ser. No. 07/872,582, entitled "Optical and Electrical Methods and Apparatus for Molecule Detection" (published Nov. 14, 1993 as International Publication No. WO93/22678, and hereinafter referred to as "the Hollis et al. application"). The Hollis et al. application is directed primarily to biosensory devices comprising an array of test sites which may be electronically addressed using a plurality of conductive leads. Various types of biosensors are described for use at the test sites, and it is suggested that the test sites may be formed in a semiconductor wafer using photolithographic processing techniques. It is further suggested that the test sites may be coupled to associated detection circuitry via transistor switches using row and column addressing techniques employed, for example, in addressing dynamic random access memory (DRAM) or active matrix liquid crystal display (AMLCD) devices.

In addition to the biosensor devices described above, several devices capable of delivering an electrical stimulus (or signal) to a selected location (or test site) within a solution or elsewhere, have been developed. As shown in FIG. 2, these devices often include a source 6, such as a current, voltage or power source, an electrode 7 coupled to the current source 6, a permeation layer 8 formed on one surface of the electrode 7, and a biologic attachment layer 9 formed upon the permeation layer 8. The permeation layer 8 provides for free transport of small counter-ions between the electrode 7 and a solution (not shown), and the attachment layer 9 provides for coupling of specific binding entities.

Exemplary systems of the type described above are disclosed in PCT Application No. PCT/US94/12270, which was published in May 1995, and is entitled "Self-Addressable Self-Assembling Microelectronic Systems and Devices for Molecular Biological Analysis and Diagnostics," and PCT Application No. PCT/US95/08570, which was published on Jan. 26, 1996, and is entitled "Self-Addressable Self-Assembling Microelectronic Systems and Devices for Molecular Biological Application," (hereinafter "the Heller et al. applications") both of which are hereby incorporated by reference. The Heller et al. applications describe electronic devices which may be fabricated using microlithographic or micromachining techniques, and preferably include a matrix of addressable micro-locations on a surface thereof. Further, individual micro-locations are configured to electronically control and direct the transport and attachment of specific binding entities (e.g., nucleic acids, antibodies, etc.) to itself. Thus, the disclosed devices have the ability to actively carry out controlled multi-step and multiplex reactions in microscopic formats. Applicable reactions include, for example, nucleic acid hybridizations, antibody/antigen reactions, clinical diagnostics, and multi-step combinational biopolymer synthesis reactions.

Additional electronic systems for interfacing with various solutions and/or biologic entities are disclosed in European Patent Application No. 89-3133379.3, published Apr. 7, 1990 and entitled "Electrophoretic System;" U.S. Pat. No. 5,378,343, issued Jan. 3, 1995 and entitled "Electrode Assembly Including Iridium Based Mercury Ultramicroelectrode Array;" U.S. Pat. No. 5,314,495, issued May 24, 1995 and entitled "Microelectronic Interface;" and U.S. Pat. No. 5,178,161, issued Jan. 12, 1993 and entitled "Microelectronic Interface."

Those skilled in the art will appreciate, however, that conventional electronic systems for carrying out and/or monitoring biologic reactions (including the devices described in the above-referenced patents and patent applications) are often bulky, expensive and, at times, difficult to control. Moreover, those skilled in the art will appreciate that, because conventional biologic systems often utilize "off-chip" circuitry to generate and control the current/voltage signals which are applied to an array of test sites, it is often difficult without the use of special equipment to precisely control the current/voltage signals generated at particular test sites. As for those conventional systems which do employ "on-chip" circuitry to generate and control the current/voltage signals which are applied to an array of test sites, in certain cases substantial difficulties have been encountered where it is desired to provide separate and distinct stimuli to selected electrode sites within a large array. One reason for this is that, when single site stimulus specificity is desired within conventional biosensor arrays, that need is often satisfied through the provision of independent signal lines for each electrode site within the array.

As a result, conventional biologic systems are often more cumbersome and expensive than is desirable.

In view of the above-noted limitations of conventional biologic systems, it is submitted that an improved biologic system which utilizes a minimum of "off-chip" circuitry and enables the use of large arrays of electrode sites while providing for very precise control of the voltages/currents delivered at a given electrode site, would be both useful and desirable.

SUMMARY OF THE INVENTION

The present invention is directed to the design, implementation and use of improved electronic systems and devices for carrying out and/or monitoring biologic reactions.

In one innovative aspect, a biologic electrode array in accordance with the present invention may comprise a matrix of electrode sites, wherein each electrode site comprises an electrode which is coupled to a respective sample-and-hold circuit via an amplifier circuit (or driving element). The number of electrode sites can range from several to at least hundreds of thousands. Each location represents a totally independent reaction site. In a preferred form, the electrodes, amplifiers and sample-and-hold circuits are integral and form an array within a single semiconductor chip, such that each sample-and-hold circuit may be loaded with a predefined voltage provided by a single, time-shared digital-to-analog converter (DAC). Further, all of the sample-and-hold circuits may be accessed through a multiplexer which may be scanned through some or all of the electrode locations. In this embodiment, each sample-and-hold circuit may comprise a capacitor and a transistor switching circuit, the transistor switching circuit, when enabled, providing electrical communication between the capacitor and a source line formed in the matrix. However, in alternative embodiments, the sample-and-hold circuits may comprise some other type of memory which may be addressed and loaded with a signal (or value) indicative of a characteristic of an electrical stimulus to be applied at an associated electrode. Such alternative memories may include electrically erasable programmable read only memory (EEPROM) cells used as an analog memory (e.g., as in the non-volatile analog signal storage chips produced by Information Storage Devices, Inc., of San Jose, Calif.), or other types of circuits capable of storing control information and producing proportional analog output values.

In another innovative aspect, a biologic electrode array in accordance with the present invention may comprise a single semiconductor chip having formed thereon a memory (for example, a random access memory (RAM)), a digital-to-analog converter (DAC) coupled to the memory, a counter, a row decoder coupled to the counter and to the memory, a column decoder coupled to the counter and to the memory, and a matrix of active biologic electrode sites coupled to the row decoder and the column decoder. In use, binary values representing voltages to be applied at the various electrode sites within the array are stored in the memory using, for example, an external computer. Then, for each address (or a selected number of addresses) within the array a binary value is read out of the memory and provided to the DAC which, in turn, converts the binary value to a voltage to be stored on the "hold" capacitor at a selected address. Once all of the addresses of the array (or the selected number of addresses) have been scanned in this fashion, the process may be repeated using either the same values initially stored in the memory or new values depending upon whether or not time variation of the voltages/currents provided at the various electrode sites is desired. Those skilled in the art will appreciate that the scanning process should be repeated often enough such that the decay over time of the stored voltages on the sample-and-hold circuits (due to unavoidable leakage currents) does not result in an unacceptable voltage/current errors at the electrodes. If non-volatile sample-and-hold circuits are used (i.e., if EEPROM or some equivalent technology is utilized), such decays may not be significant, allowing for arbitrarily slow update rates.

In an alternative embodiment, the memory, counter and DAC may be disposed on one or more separate chips.

In view of the foregoing, it will be appreciated that a biologic array in accordance with the present invention provides for very precise control of the potentials/currents delivered to individual electrodes within the array, while minimizing the utilization of "off-chip" circuitry and overall system costs. Further, by using local sample-and-hold circuits (or other local memory circuits) to control the level of electrical stimulus applied to particular test sites, arrays in accordance with the present invention may achieve a level of stimulus specificity and electrode utilization far superior to that achieved using most prior art systems.

In another innovative aspect, the present invention provides for the fabrication of an entire active array surface on a thermally-isolated membrane containing on-board, controllable heating elements. By cycling the temperature of the heating elements, it is possible to perform DNA amplification in situ, for example, by the polymerase chain reaction.

In still another innovative aspect, the present invention provides for the incorporation of optical fluorescence or absorption detection circuitry within a biologic electrode array matrix to improve coupling of emitted photons into the detection electronics. More specifically, in accordance with one embodiment of the present invention, a biologically active electrode is formed above a suitable optical detector such as a MOS-photodiode structure within, for example, a CMOS circuit. In such an embodiment, the electrode may be formed from a substance which is at least partially transparent, or the electrode may be formed in such a fashion that it permits the passage of light through its body to an underlying photodetector.

In yet another embodiment of the invention, a method of addressing and driving a biological electrode array includes the steps of providing a chip having an array of electrodes, each electrode being associated with a local memory, addressing one or more electrodes within the array using a plurality of row and column lines, wherein each addressable electrode is connectable to a single row line and a single column line. The method further includes the steps of storing a value in the local memory of each addressed electrode representative of a voltage that is to be applied to each electrode and driving the addressed electrodes at the voltage corresponding to the stored values.

In still another embodiment of the invention, a method of addressing and driving a biological electrode array includes the steps of providing a chip having an array of electrodes, each electrode being associated with a driving element, addressing one or more electrodes within the array using a plurality of row and column lines, wherein each addressable electrode is connectable to a single row line and a single column line, and selectively coupling the driving element of the one or more addressed electrodes with a voltage line so as to charge the addressed electrode with the voltage on the voltage line.

According to another embodiment of the invention, a method of carrying out biological reactions on a biologic electrode array includes the steps of providing a chip having an array of electrodes, each electrode being associated with a local memory. A reaction medium including reactants is provided within close proximity of the array of electrodes. One or more electrodes within the array are addressed using a plurality of row and column lines, wherein each addressable electrode is connectable to a single row line and a single column line. A value is stored in the local memory of each addressed electrode representative of a voltage that is to be applied to each addressed electrode. The one or more addressed electrodes are then driven at the voltage corresponding to the stored values, whereby the electrical field created at the one or more electrodes is used to react the reactants contained in the reaction medium at a location adjacent to the electrode.

In yet another embodiment, a method of carrying out biological reactions on a biologic electrode array includes the step of providing a chip having an array of electrodes, each electrode being associated with a driving element. A reaction medium is provided within close proximity of the array of electrodes. One or more electrodes within the array are addressed using a plurality of row and column lines, wherein each addressable electrode is connectable to a single row line and a single column line. A driving element is selectively coupled to the one or more addressed electrodes with a voltage line so as to charge the addressed electrode with the voltage on the voltage line, whereby the electrical field created at the one or more electrodes is used to react the reactants contained win the reaction medium at a location adjacent to the electrode.

In still another embodiment, a biologic electrode array comprises a semiconductor substrate, a matrix of electrode sites disposed on the semiconductor substrate, a local memory coupled to each electrode site, row and column decoders for addressing the electrode sites using a plurality of row and column lines, a data line for delivering to the local memory a value indicative of a characteristic of an electrical stimulus to be applied at the electrode site, and a driving element located at each electrode site, the driving element delivering the electrical stimulus to each electrode site in response to the stored value in the local memory.

In view of the foregoing, it is an object of the present invention to provide an improved biologic electrode array for carrying out and controlling multi-step and multiplex reactions in microscopic formats.

It is another object of the present invention to provide an improved biologic electrode array which is compact and minimizes the utilization of off-chip control circuitry, even for large numbers of electrodes.

It is another object of the present invention to provide an improved biologic electrode site which includes a sample-and-hold circuit, and which may be fabricated using conventional CMOS semiconductor fabrication techniques.

It is still another object of the present invention to provide an improved biologic electrode array which includes heating elements for enhancing the progression of reactions such as DNA amplification in situ.

It is still another object of the present invention to provide an improved biologic array which includes a plurality of optical detectors formed beneath selected electrode sites.

It is another object of the present invention to provide a device and method for the combinatorial synthesis of biopolymers, such as, for example, oligonucleotides and peptides.

DETAILED DESCRIPTION OF PREFERRED EMBODIMENTS

Figure 1:
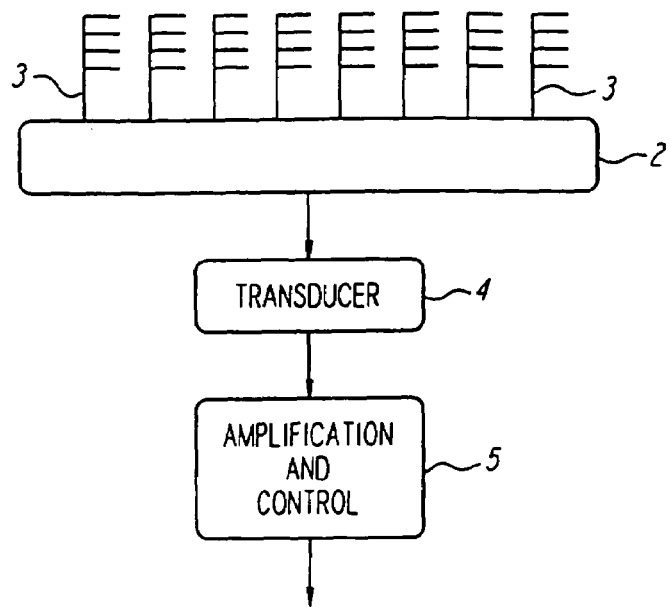
FIG. 1 is an illustration of a prior art passive biologic system.
Figure 2:
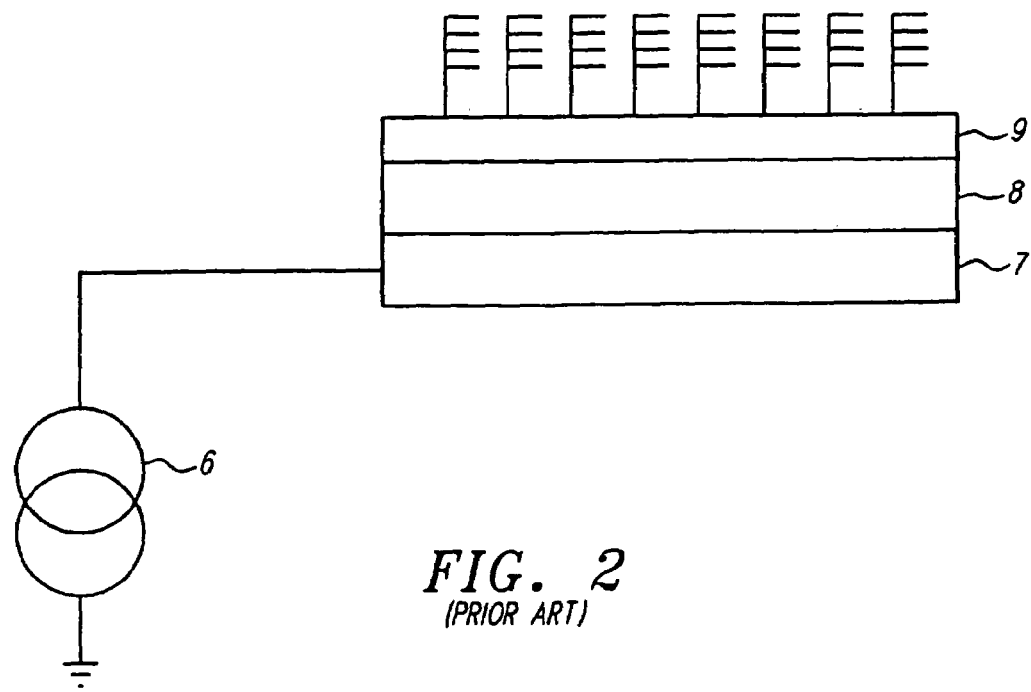
FIG. 2 is an illustration of a prior art active biologic system.
Figure 3:
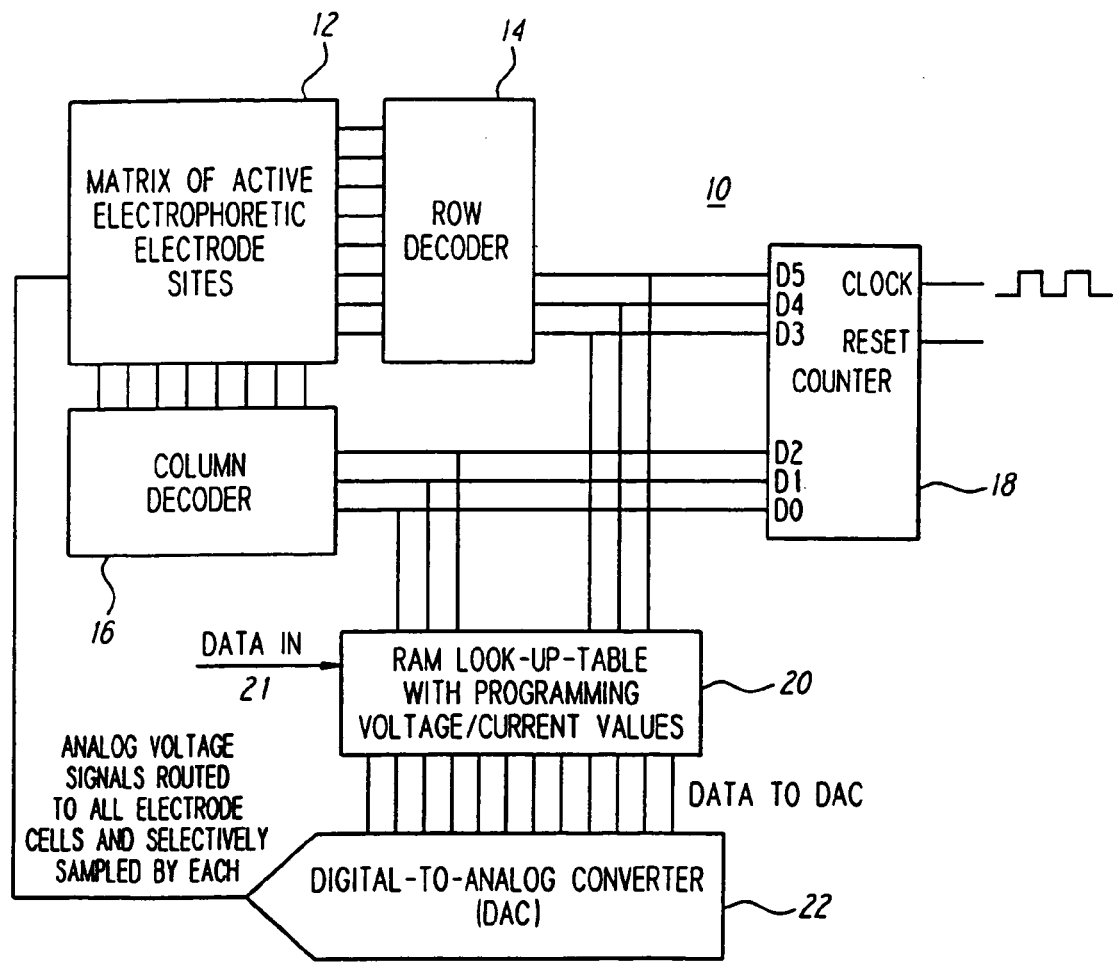
FIG. 3 is an illustration of a biologic array in accordance with one form of the present invention.

Turning now to the drawings, as shown in FIG. 3, a biologic array 10 in accordance with one preferred form of the present invention may comprise a matrix of active biologic electrode sites 12, a row decoder 14, a column decoder 16, a counter 18, a random access memory (RAM) 20 acting as a look-up table, and a digital-to-analog converter (DAC) 22. In a preferred form, each of the above listed elements may be disposed on a single semiconductor chip, and the entire array 10 may be fabricated using conventional CMOS semiconductor fabrication techniques. Further, in the presently preferred form a computer (not shown) may be used to load data, as needed, into the RAM 20 via, for example, a data input port 21.

Figure 4A:
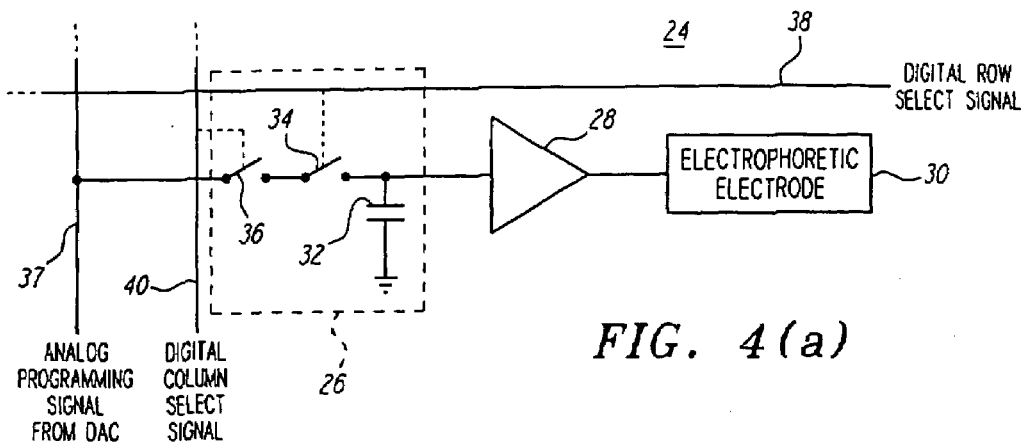
FIG. 4(a) is an illustration of a biologic electrode site in accordance with one form of the present invention.

Turning now also to FIG. 4(a), each biologic electrode site 24, which makes up the matrix of biologic electrodes 12, may comprise a sample-and-hold circuit 26, an amplifier 28 and an electrode 30. In one preferred form, the sample-and-hold circuit 26 may comprise a capacitor 32 and two transistor switches 34 and 36. The switches 34 and 36 are connected in series and, when closed, provide electrical communication between a voltage source line 37 (coupled to the DAC 22) and the capacitor 32. The switches 34 and 36 are coupled, respectively, to a designated row select line 38 and column select line 40 formed within the matrix 12.

Figure 4B:
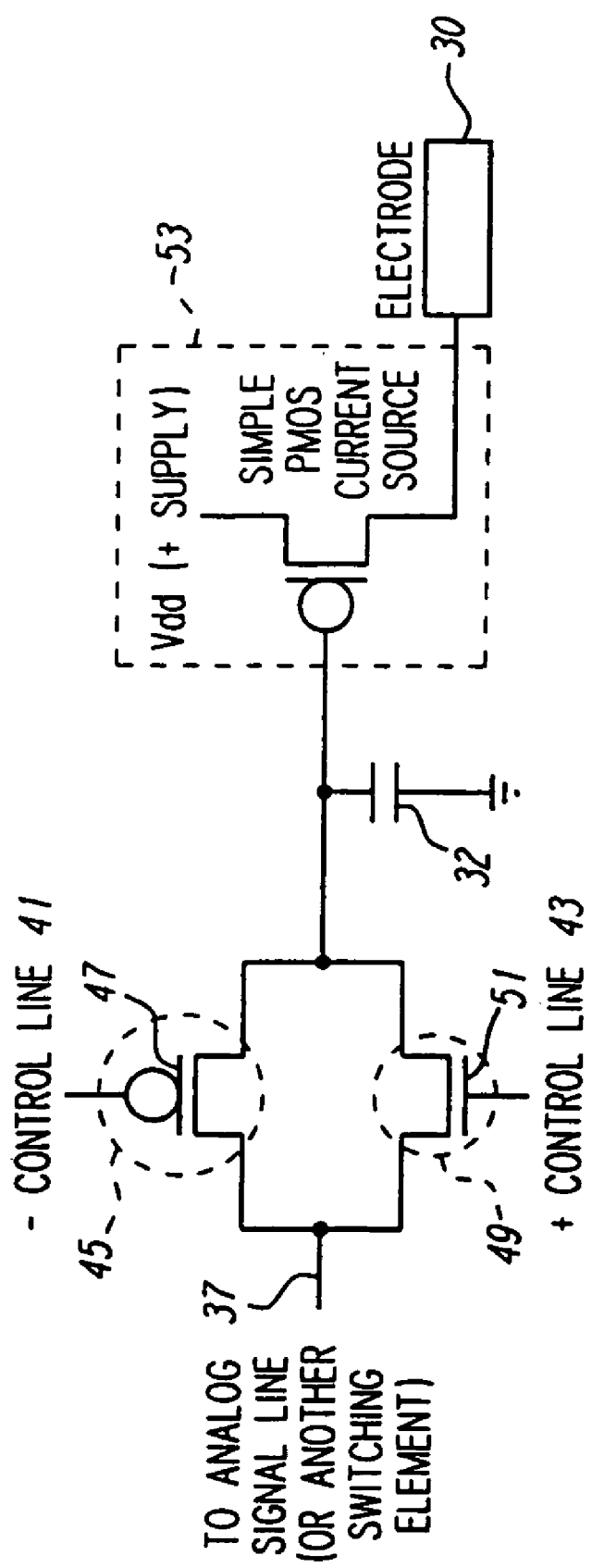
FIG. 4(b) is a circuit diagram showing in more detail one of the switching circuits and the amplifier circuit of the biologic electrode site illustrated in FIG. 4(a).
Figure 4C:
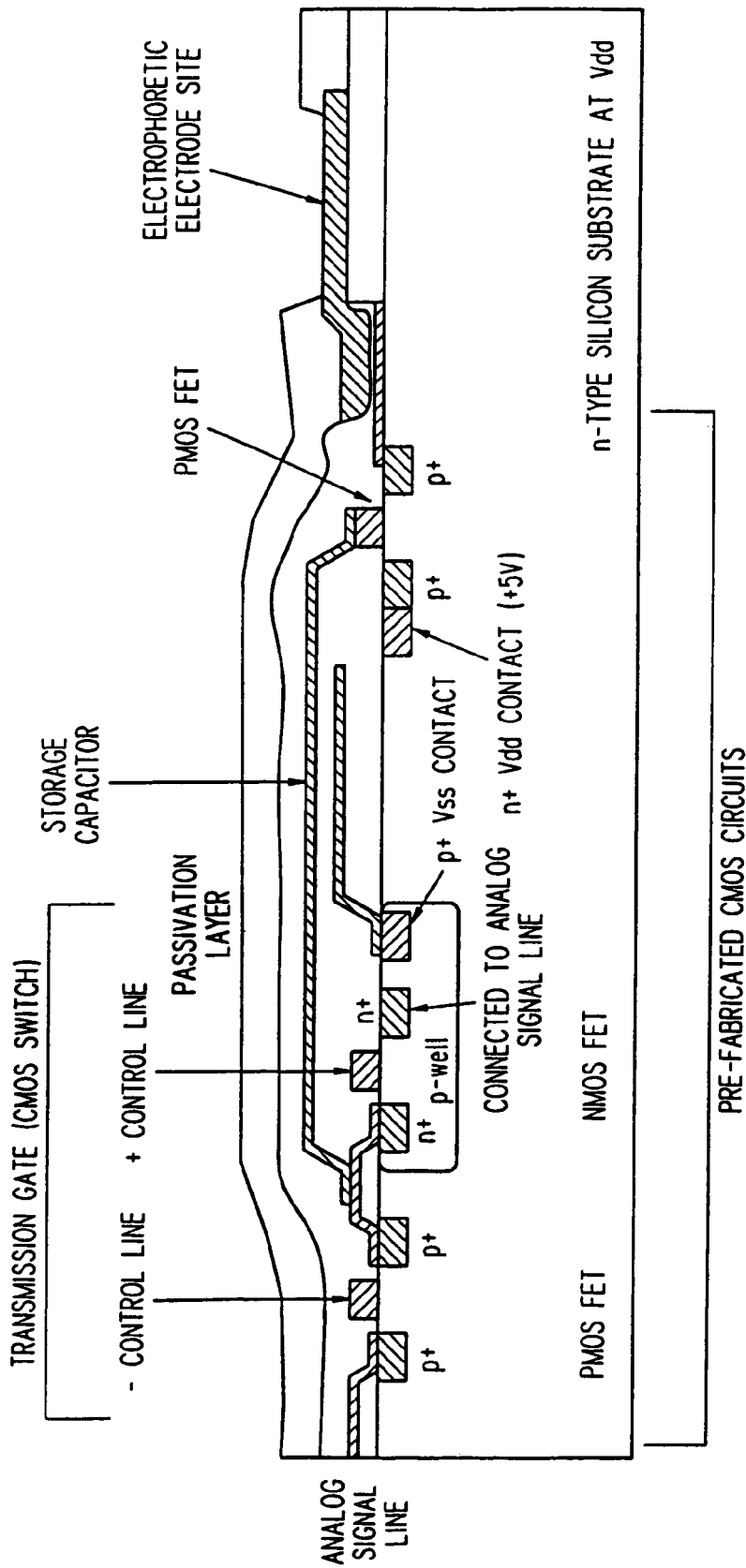
FIG. 4(c) illustrates how those portions of the electrode site illustrated in FIG. 4(b) might be fabricated using CMOS circuitry.

As shown in FIGS. 4(b) and 4(c), each row select line 38 and each column select line 40 may comprise, for example, a positive control line (+control line) 41 and a negative control line (−control line) 43, and each switch 34 or 36 may comprise a CMOS transmission gate, i.e., a PMOS FET 45 having a gate region 47 coupled to the negative control line 43 and a NMOS FET 49 having a gate region 51 coupled to the positive control line 41. In addition, the amplifier circuit (or driving element) 28 may comprise a PMOS current source 53.

In an alternative embodiment, a single switch, such as that described above, may be controlled by a two input logic gate (e.g., an AND or NAND gate) with complementary outputs (e.g., a +control line and −control line), and may be used to selectively connect the capacitor 32 to the voltage source line 37. In such an embodiment, the logic gate would respond to a coincidence of signals on the row and column select lines 38 and 40, respectively. Further, it may be noted that in some instances a two transistor transmission gate will not be needed, and a single MOS transistor can be used as a switch. In such a case, the logic gate need only provide a single output to the switch.

The design, fabrication and function of counters, row decoders, column decoders, digital-to-analog converters, and random access memories are well known in the art and, thus, the structure and operation of those elements are not discussed in detail herein. Rather, a general description of the function of the biologic electrode array 10 is provided below.

In use, binary values representing voltages to be applied at the various electrode sites 24 within the matrix 12 are stored in the RAM 20 (or other suitable memory device) using, for example, an external computer. Then, for each address (or a selected number of addresses) within the matrix 12 a binary value is read out of the RAM 20 and provided to the DAC 22 which, in turn, converts the binary value to a voltage to be stored on the capacitor 32 located at the selected site address. An output amplifier 28 is coupled between the capacitor 32 and the electrode 30 and provides an amplified stimulus signal to the electrode 30. The output amplifier 28 may comprise a voltage amplifier and/or buffer and may thus amplify the voltage on the capacitor 32 and provide an amplified voltage to the electrode 30. Alternatively, the output amplifier 28 may comprise a current output amplifier (for example, a transconductance amplifier) and provide a current signal to the electrode 30. Once all of the addresses of the matrix (or the selected number of addresses) have been scanned in this fashion, the process may be repeated using either the same values initially stored in the RAM 20 or new values, depending upon whether or not time variation of the voltages/currents provided at the various electrode sites is desired. Those skilled in the art will appreciate that the scanning process should be repeated often enough such that the decay over time of the stored voltages on the capacitors 32 (due to unavoidable leakage currents) does not result in an unacceptable voltage/current error at the electrodes 30.

In equivalent and alternative forms, the counter 18, RAM 20, and DAC 22 may be placed on or off of the chip comprising the electrophoretic electrode array, as a matter of design choice, and if desired, some other type of circuit (for example, a simple counter or shift register) may be used to control the sequential loading of the sample-and-hold circuits 26 located at the respective electrode sites 24.

Figure 5:
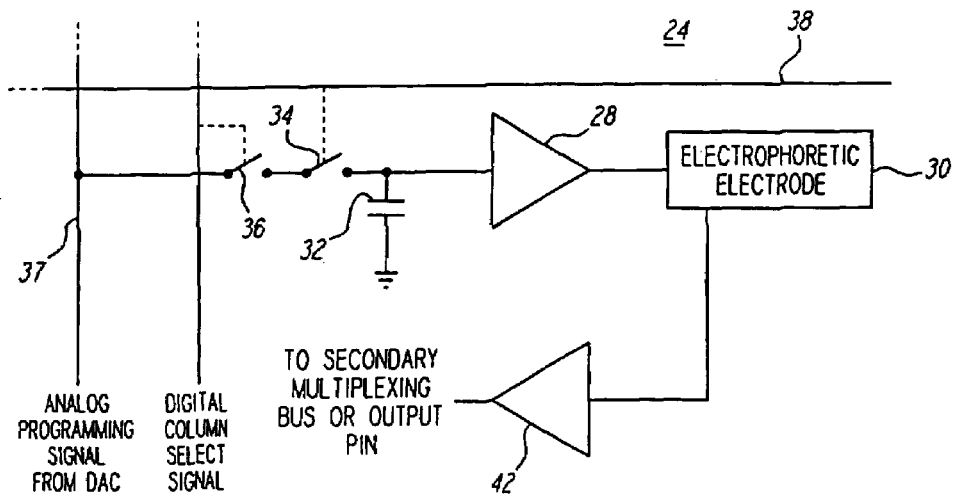
FIG. 5 is an illustration of a biologic electrode site which includes circuitry for monitoring an electrical characteristic of an electrode located at the site.

Turning now also to FIG. 5, for some applications it may be desirable to provide for monitoring of the condition (or electrical characteristics) of one or more of the electrodes 30 within the matrix 12. In this case, it is assumed that if the electrode is driven with a known current, the voltage that develops is sensed, or, if the electrode is driven with a known voltage, the current that flows is sensed. To allow monitoring of the condition of a given electrode 30 a voltage sense amplifier 42 may be coupled to the electrode 30 and to a secondary multiplexing bus or output pin (not shown). The voltage sense amplifier 42 provides an indication of the voltage at the electrode 30 relative to an electrical ground (not shown) for the entire array or relative to a selected reference electrode (not shown) on the array. The voltage of the reference electrode may, in some instances, also be the ground used for the array. It should be noted that the output of the sense amplifiers 42 for the electrode sites 24 in the array may also be multiplexed onto a common sense signal line, and that the signals provided to the common sense signal line may be de-multiplexed using conventional circuitry, such as a sample-and-hold circuit (not shown) and an analog-to-digital converter (not shown). The common sense signal line may be separate from the common signal line (i.e., the voltage source line 37), or it may be same line, in which case, it would be time shared, serving for some selected periods of time to provide charging signals to the capacitors 32 of the electrode sites 24, and serving for other periods of time as a carrier for sense signals generated at the electrode sites 24.

In the case where the electrodes 30 are driven by voltage amplifiers 28 and the current that flows through the electrode 30 is to be sensed, a sense resistor (not shown) may be connected between the output of the voltage amplifier 28 and the electrode 30, and two inputs of a differential amplifier circuit (not shown) may be connected across the sense resistor. In such an embodiment, the signal generated at the output of the differential amplifier will be proportional to the current flowing through the electrode 30.

As explained to some extent above, while the embodiments illustrated in FIGS. 4(a) and 5 employ two switches 34 and 36 connected in series to control the loading of the capacitor 32 (one switch being controlled by each of the row, and column lines, respectively) those skilled in the art will appreciate that the switching function may be implemented in any of a number of ways. For example, it would be considered equivalent to replace the switches 34 and 36, shown in FIGS. 4(a) and 5, with CMOS transmission gates or a combination of an AND gate and a switch.

Turning again to FIG. 4(c), in a preferred form the biologic array 10 may be fabricated using a CMOS or other active circuit process. Moreover, those skilled in the art will appreciate that completely fabricated CMOS circuitry embodying some or all of the above-described functions may be post-processed to form the complete active biologic electrode array 10 described above. For example, as illustrated in FIG. 6, the biologic electrodes 30 may be disposed atop the underlying CMOS circuitry and then protected with an overlapping passivation layer 44. Further, openings in the passivation layer 44 may be fabricated to expose the active regions of the biologic electrodes 30 as well as any required peripheral interconnection sites, e.g., bond-pads (not shown). In such an embodiment, the electrodes 30 may be fabricated from electrochemically suitable materials, such as gold, iridium or platinum, and may be deposited and patterned using conventional thin-film deposition techniques. The passivation layer 44 may comprise, for example, plasma-deposited silicon nitride and/or silicon carbide, and openings in the passivation layer 44 may be formed using conventional microfabrication techniques such as plasma etching. Finally, if biomolecules are to be bound on or near the surface of the electrodes 30, coupling agents and/or intermediate layers (shown in FIG. 7) may be used.

Figure 6A:
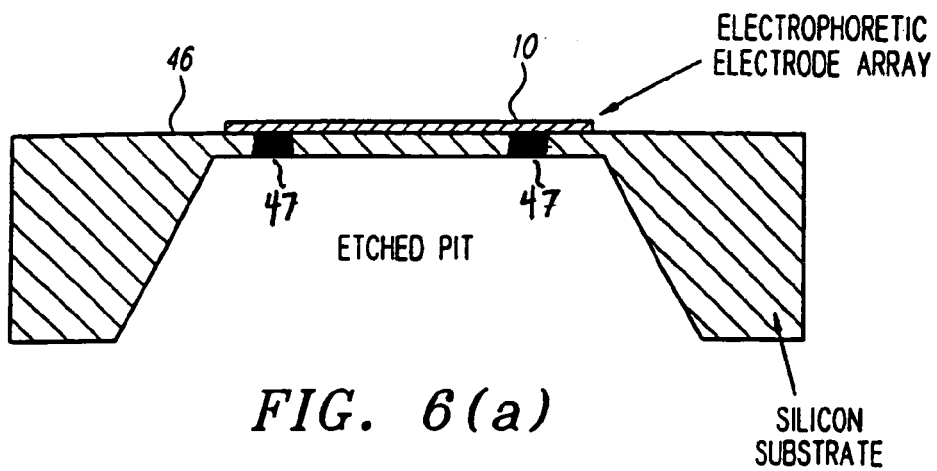
FIG. 6(a) illustrates the fabrication of a combined thermally isolated membrane and biologic electrode array, wherein the biologic electrode array is etched onto a back side surface of a silicon substrate.
Figure 6B:
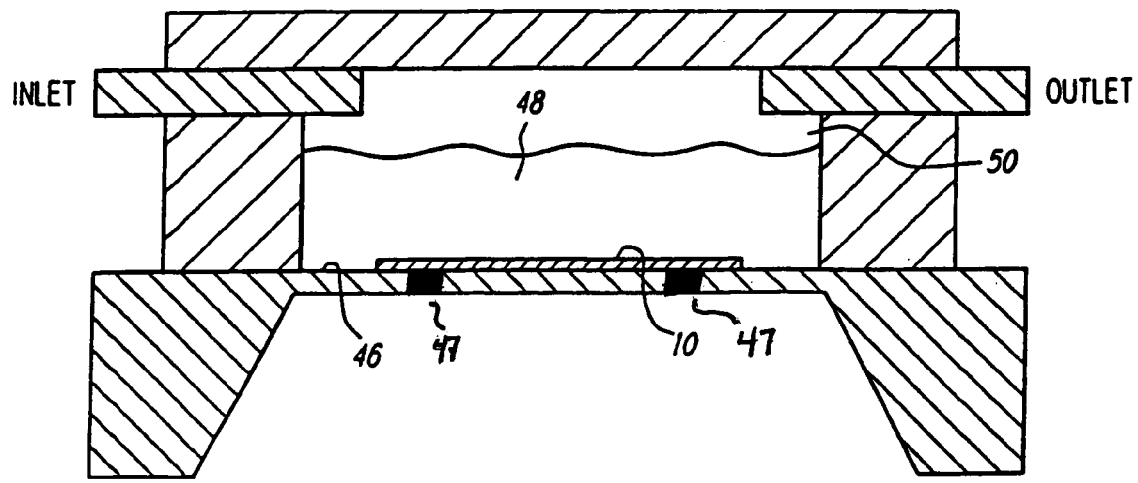
FIG. 6(b) illustrates the attachment of a low-thermal-conductivity chamber to the combined thermally isolated membrane and biologic electrode array shown in FIG. 6(a).

Turning now to FIGS. 6(a) and 6(b), in another preferred form the entire active surface of the biologic array 10 may be formed on a thermally-isolated membrane 46 containing one or more on-board, controllable heating elements 47. The thermally-isolated membrane can be formed using micromachining techniques well-known in the art. For example, the back-side of the completed CMOS waver containing the biologic array circuitry and electrodes can be coated with a suitable etch mask (e.g., silicon nitride). The silicon nitride is patterned using standard techniques to form openings where the membrane is to be formed. The membranes are formed by submerging the wafer in an etching solution (e.g., tetramethylammononium hydroxide loaded with dissolved silicon, as described in Klassen, et al., "Micromachined Thermally Isolated Circuits," Proceedings of the Solid-State Sensor and Actuator Workshop, Hilton Head, S.C., Jun. 3–6, 1996, pp. 127–131). The membrane can thus be temperature cycled to allow DNA amplification in situ. Further, controllable heating of the membrane maybe accomplished through the use of an array of resistors or appropriately biased MOSFETS (metal oxide semiconductor field effect transistors) distributed throughout the membrane area. Thus, if a solution 48 (shown in FIG. 6(*b*)) overlying the array 10 is provided with DNA and suitable chemicals to carry out a polymerase chain reaction (PCR) to amplify the DNA, cycling the temperature of the membrane will allow the desired amplification. If thermal feedback is desired, the temperature of the membrane may be readily determined. For example, the temperature coefficient of resistance of the heater resistors or the forward voltage of diodes incorporated into the membrane may be utilized to provide an indication of the solution temperature. Finally, once the DNA contained within the solution 48 is amplified, appropriate chemicals may be injected into the chamber 50 to effect one or more desired analysis steps. Examples of such chemicals are restriction enzymes, fluorescent labels and intercalcators, etc.

An exemplary micromachined, membrane-based DNA amplification system has been demonstrated by Northrup, et al. (see Northrup et al., "DNA Amplification with a Microfabricated Reaction Chamber," Proceedings of Transducers '93, the 7th International Conference on Solid State Sensors and Actuators, Yokohama, Japan, Jun. 7–10, 1993, pp. 924–926, which is incorporated herein by reference) and, thus, the specific structure and operation of the membrane-based DNA amplification system is not discussed herein in detail. However, it should be noted that the Northrup et al. system provides merely for thermal cycling, and has no analysis or biologic electrode control capabilities. Thus, it is believed that those skilled in the art will find a biologic array in accordance with present invention to be highly advantageous, as such an array allows for in situ DNA amplification and subsequent analysis using a single device.

Figure 7:
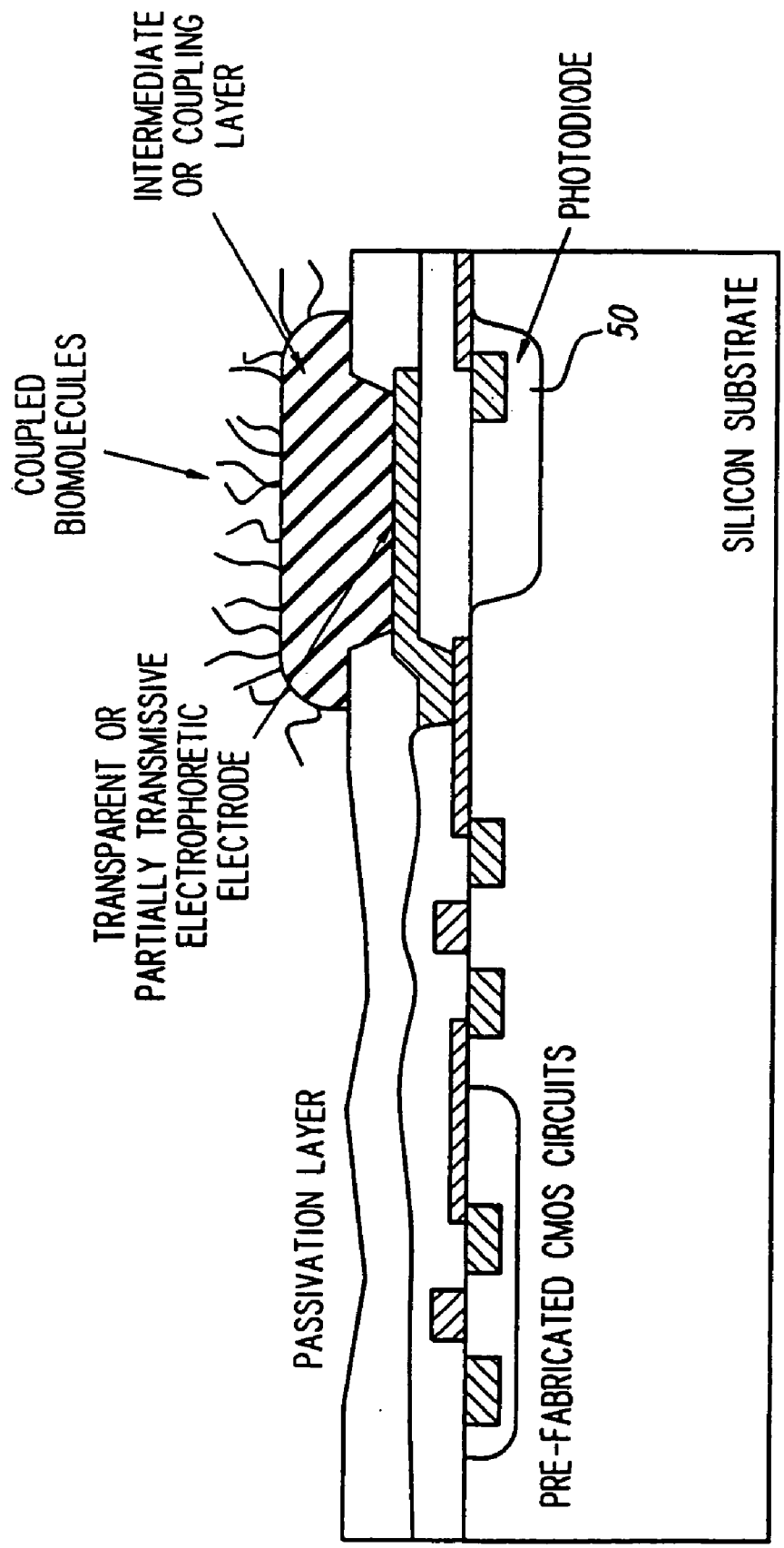
FIG. 7 illustrates a biologic electrode site including an optical detector in accordance with the present invention.
Figure 8A:
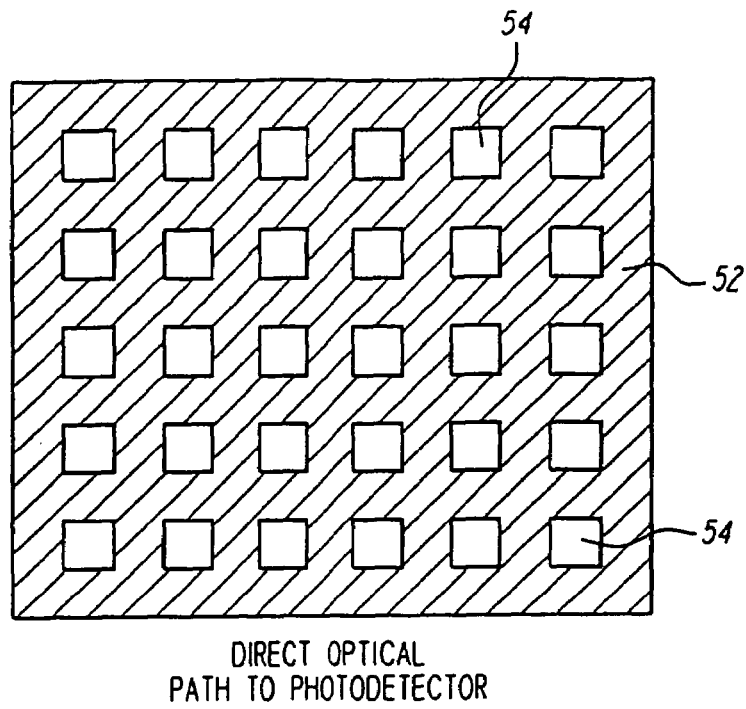
FIG. 8(a) is a top view of a punctuated, partially transparent electrode in accordance with one form of the present invention.
Figure 8B:
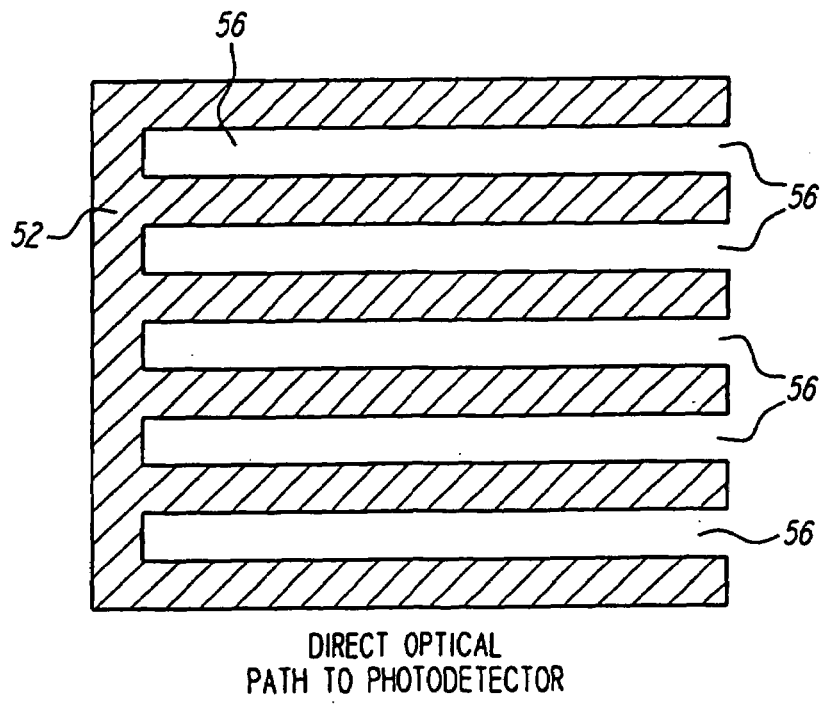
FIG. 8(b) is a top view of an alternative embodiment of a partially transparent electrode in accordance with the present invention.

Turning now to FIG. 7, for some applications, it may be desirable to incorporate optical fluorescence or transmittance detection circuitry directly into the electrode matrix 12 to improve coupling of emitted or transmitted photons into any provided detection electronics. In the case of fluorescence detection, the entire array would be illuminated with light at wavelength(s) known to excite fluorescence in the fluorescently labeled biomolecules such as DNA or intercalators between DNA strands. This light would be detected by the optical detection means located at each site. In the case of transmittance detection, the entire array would be illuminated with light at wavelength(s) known to be attenuated by the presence of the biomolecules of interest (i.e., the light at those wavelengths is absorbed by the biomolecules) the presence of the biomolecules of interest at a given electrode site would be detected by an attenuation of the light sensed by the optical detector local to that site. This approach can greatly improve the signal-to-noise ratio (SNR) over the use of an imaging camera remote to the biologic-array 10. In essence, this involves combining a biologically active electrode (with or without active multiplexing circuitry) above a suitable optical detector 50 such as a MOS-photodiode or a charge-coupled device (CCD) structure. In such an embodiment, it may be desirable to utilize transparent electrodes, such as those formed from indium tin oxide (ITO), or it may be desirable to utilize a slitted or punctuated electrode structure, such as that shown in FIGS. 8(*a*) and 8(*b*). By providing orifices 54 (as shown in FIG. 8(*a*)) or troughs 56 (shown in FIG. 8(*b*)) through the surface of the electrode 52 it is possible to allow the passage of light through the electrode 52 to the optical detector 50. Those skilled in the art will appreciate that-by eliminating the need for an external camera and retaining the ability to perform biologically-controlled hybridizations (or other molecular interactions), the overall cost of a complete analysis system can be greatly reduced.

With respect to combinatorial synthesis, the device allows very large numbers of sequences to be synthesized on the array. The basic concept for combinatorial synthesis involves the use of free field electrophoretic transport to deliver, concentrate, and react monomers, coupling reagents, or deblocking reagents at specific addressable electrode sites on the device. The concept capitalizes on the inherent ability of the device to electronically protect other electrode sites on the device.

While the invention of the subject application may take several alternative and equivalent forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

What is claimed is:

1. A method of addressing and driving a biologic electrode array comprising the steps of:
providing a chip having an array of electrodes formed on a thermally-isolated membrane having at least one controllable heating element, each electrode being associated with a local memory;
addressing one or more electrodes within the array using a plurality of row and column lines, wherein each addressable electrode is connectable to a single row line and a single column line;
storing a value in the local memory of each addressed electrode representative of a voltage that is to be applied to each addressed electrode; and
driving the addressed electrodes at the voltage corresponding to the stored values.

2. The method of claim 1 wherein the local memory stores a binary value representing a voltage to be applied to the addressed electrode.

3. The method of claim 1 wherein the addressing step is performed using a row decoder and a column decoder.

4. The method of claim 1 wherein the local memory is an EEPROM.

5. A method of addressing and driving a biologic electrode array comprising the steps of:
providing a chip having an array of electrodes formed on a thermally-isolated membrane having at least one controllable heating element, each electrode being associated with a driving element;
addressing one or more electrodes within the array using a plurality of row and column lines, wherein each addressable electrode is connectable to a single row line and a single column line;

selectively coupling the driving element of the one or more addressed electrodes with a voltage line so as to charge the addressed electrode with the voltage on the voltage line.

6. The method of claim 5 wherein the voltage applied to the voltage line is changed between different voltages.

7. A method of carrying out biological reactions on a biologic electrode array comprising the steps of:
providing a chip having an array of electrodes formed on a thermally-isolated membrane having at least one controllable heating element, each electrode being associated with a local memory;
providing a reaction medium including reactants within close proximity of the array of electrodes;
addressing one or more electrodes within the array using a plurality of row and column lines, wherein each addressable electrode is connectable to a single row line and a single column line;
storing a value in the local memory of each addressed electrode representative of a voltage that is to be applied to each addressed electrode;
driving the one or more addressed electrodes at the voltage corresponding to the stored values, whereby the electrical field created at the one or more electrodes is used to react the reactants contained in the reaction medium at a location adjacent to the electrode; and
cycling the temperature of at least one controllable heating element.

8. The method according to claim 7 wherein the reactants are nucleic acids.

9. The method according to claim 8 wherein the reaction synthesizes oligonucleotides.

10. The method according to claim 9 wherein an array of oligonucleotides is synthesized proximal to a surface of the chip containing the array of electrodes.

11. The method according to claim 7 wherein the reactants are amino acids.

12. The method according to claim 11 wherein the reaction synthesizes peptides.

13. The method according to claim 7 wherein the reaction comprises deprotecting a reactant disposed proximal to the charged electrode.

14. The method according to claim 7 wherein the one or more electrodes are positively charged so as to hydrolyze water.

15. A method of carrying out biological reactions on a biologic electrode array comprising the steps of:
providing a chip having an array of electrodes formed on a thermally-isolated membrane having at least one controllable heating element, each electrode being associated with a driving element;
providing a reaction medium including reactants within close proximity of the array of electrodes;
addressing one or more electrodes within the array using a plurality of row and column lines, wherein each addressable electrode is connectable to a single row line and a single column line;
selectively coupling the driving element of the one or more addressed electrodes with a voltage line so as to charge the addressed electrode with the voltage on the voltage line, whereby the electrical field created at the one or more electrodes is used to react the reactants contained in the reaction medium at a location adjacent to the electrode; and
cycling the temperature of at least one controllable heating element.

16. The method according to claim 15 wherein the reactants are nucleic acids.

17. The method according to claim 16 wherein the biological reaction synthesizes oligonucleotides.

18. The method according to claim 17 wherein an array of oligonucleotides is synthesized proximal to a surface of the chip containing the array of electrodes.

19. The method according to claim 15 wherein the reactants are amino acids.

20. The method according to claim 19 wherein the reaction synthesizes peptides.

21. The method according to claim 15 wherein the biological reaction comprises deprotecting a reactant disposed proximal to the charged electrode.

22. The method according to claim 15 wherein the one or more electrodes are positively charged so as to hydrolyze water.

23. An biologic electrode array comprising:
a semiconductor substrate having at least one controllable heating element;
a matrix of electrode sites disposed on the semiconductor substrate; a local memory coupled to each electrode site;
row and column decoders for addressing the electrode sites using a plurality of row and column lines;
a data line for delivering to the local memory a value indicative of a characteristic of an electrical stimulus to be applied at the electrode site; and
a driving element located at each electrode site, the driving element delivering the electrical stimulus to each electrode site in response to the stored value in the local memory.

24. The device of claim 23 wherein the electrical stimulus is a voltage.

25. The device of claim 23 wherein the row and column decoders are disposed on the semiconductor substrate.

26. The device of claim 23 wherein at least a portion of the array is formed using CMOS fabrication techniques.

27. The device of claim 23 further comprising a permeation layer disposed over the matrix of electrode sites.

28. The device of claim 23 wherein the data line delivers a binary value to the local memory.

* * * * *